(12) United States Patent
Paehler et al.

(10) Patent No.: US 9,968,605 B2
(45) Date of Patent: May 15, 2018

(54) 2-(2-METHYLAMINO-PYRIMIDIN-4-YL)-1H-INDOLE-5-CARBOXYLIC ACID [(S)-1-CARBAMOYL-2-(PHENYL-PYRIMIDIN-2-YL-AMINO)-ETHYL]-AMIDE FOR USE IN THE TREATMENT OF PAIN ASSOCIATED TO OSTEOARTHRITIS

(71) Applicant: SANOFI, Paris (FR)

(72) Inventors: Tobias Paehler, Frankfurt am Main (DE); Klaus Flechsenhar, Frankfurt am Main (DE); Kirsten Grothe, Frankfurt am Main (DE); Martin Lunnon, Paris (FR); Christelle Jan, Paris (FR)

(73) Assignee: Sanofi, Paris (FR)

( * ) Notice: Subject to any disclaimer, the term of this patent is extended or adjusted under 35 U.S.C. 154(b) by 0 days. days.

(21) Appl. No.: 15/322,949

(22) PCT Filed: Jun. 30, 2015

(86) PCT No.: PCT/EP2015/064794
§ 371 (c)(1),
(2) Date: Dec. 29, 2016

(87) PCT Pub. No.: WO2016/001197
PCT Pub. Date: Jan. 7, 2016

(65) Prior Publication Data
US 2017/0119765 A1 May 4, 2017

(30) Foreign Application Priority Data
Jul. 3, 2014 (EP) .................................... 14306088

(51) Int. Cl.
*A61K 31/506* (2006.01)
*C07D 403/14* (2006.01)
*C07D 403/12* (2006.01)

(52) U.S. Cl.
CPC .......... *A61K 31/506* (2013.01); *C07D 403/12* (2013.01); *C07D 403/14* (2013.01)

(58) Field of Classification Search
CPC ... C07D 403/12; C07D 403/14; A61K 31/506
See application file for complete search history.

(56) References Cited

U.S. PATENT DOCUMENTS 7,285,560 B2   10/2007   Ritzeler
7,462,638 B2   12/2008   Michaelis
8,778,955 B2   7/2014    Ritzeler
8,809,358 B2   8/2014    Michaelis
9,067,918 B2   6/2015    Ritzeler

OTHER PUBLICATIONS

Sun, B. H., et al. "New Developments in Osteoarthritis" Rheum. Dis. N. Am., 2007, 33, p. 135-148.
Wenham, C. Y. J., et al. "The Role of Synovitis in Osteoarthritis" Ther. Adv. Musculoskel. Dis., 2010, 2(6), p. 349-359.
Hayashi, D., et al. "Longitudinal assessment of cyst-like lesions of the knee and their relation to radiographic osteoarthritis and MRI-detected effusion and synovitis in patients with knee pain" Arthritis Research and Therapy 2010, 12, R172, p. 1-9.
Roman-Blas, J. A., et al. "Review NF-kB as a potential therapeutic target in osteoarthritis and rheumatoid arthritis" Osteoarthritis Cartilage, 2006, 14, p. 839-848.
D'Agostino, M. A., et al. "EULAR report on the use of ultrasonography in painful knee osteoarthritis. Part 1: Prevalence of inflammation in osteoarthritis" Ann. Rheum. Dis. 2005, 64, p. 1703-1709.
Conaghan, P., et al. "EULAR report on the use of ultrasonography in painful knee osteoarthritis. Part 2: Exploring decision rules for clinical utility" Ann. Rheum. Dis. 2005, 64, p. 1710-1714.
Buckup, K. "Clinical Tests for the Musculoskeletal System" 2008, Thieme, 2nd edition, pp. 202-203.
Bellamy, N. et al. "Validation Study of WOMAC: A Health Status Instrument for Measuring Clinically Important Patient Relevant Outcomes to Antirheumatic Drug Therapy in Patients with Osteoarthritis of the Hip or Knee" J. Rheumatology, 1988, 15, p. 1833-1840.
Martel-Pelletier, J. et al. "Future therapeutics for osteoarthritis" Bone, 2012, 51, p. 297-311.
"Safety of Single Doses of SAR113945 and Efficacy and Safety of a New Formulation Given Into the Knee in Osteoarthritis Patients | Part II—Tabular View—ClinicaiTrials.gov" Feb. 22, 2013 URL:http://clinicaltrials.gov/ct2/show/record/NCT01598415?
European Search Report for European Application No. EP 14 30 6088, dated Sep. 1, 2014, p. 1-6.
International Search Report for International Application No. PCT/EP2015/064794, completed Jul. 28, 2015, dated Aug. 10, 2015, p. 1-11.
Grothe, K. et al. "IkB kinase inhibition as a potential treatment of osteoarthritis e results of a clinical proof-of-concept study" Osteoarthritis and Cartilage, 25, 2017, 46-52.
Sanofi, "Q3 2013 Marks the End of the Patent Cliff Period" Press Release, Paris, France, Oct. 30, 2013.

*Primary Examiner* — Deepak R Rao
(74) *Attorney, Agent, or Firm* — McDonnell Boehnen Hulbert & Berghoff

(57) ABSTRACT

2-(2-methylamino-pyrimidin-4-yl)-1H-indole-5-carboxylic acid [(S)-1-carbamoyl-2-(phenyl-pyrimidin-2-yl-amino)-ethyl]-amide for use in the treatment of pain associated with osteoarthritis in the knee.

17 Claims, 2 Drawing Sheets

Figure 1:
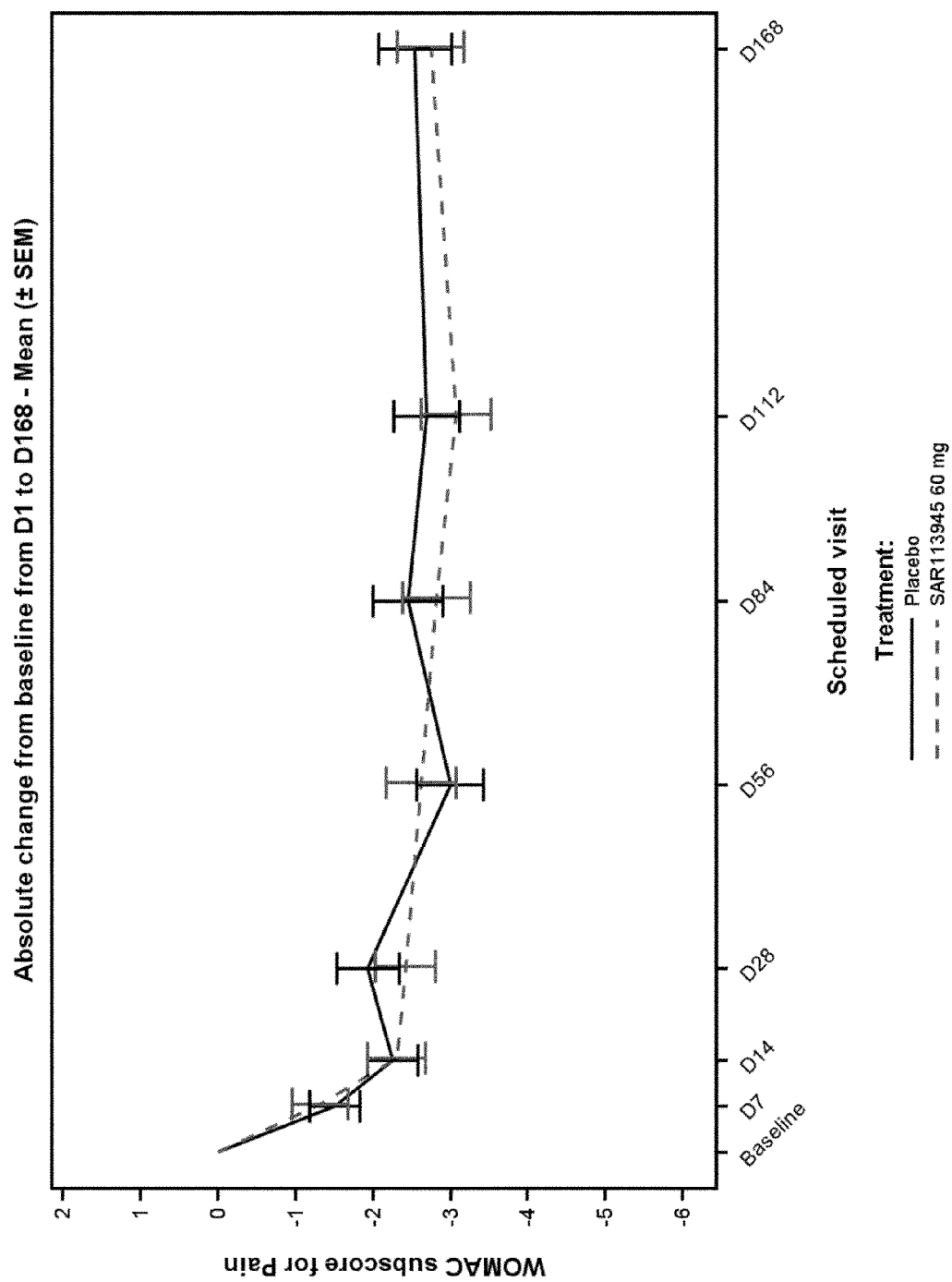

2-(2-METHYLAMINO-PYRIMIDIN-4-YL)-1H-INDOLE-5-CARBOXYLIC ACID [(S)-1-CARBAMOYL-2-(PHENYL-PYRIMIDIN-2-YL-AMINO)-ETHYL]-AMIDE FOR USE IN THE TREATMENT OF PAIN ASSOCIATED TO OSTEOARTHRITIS

This application is a national stage application under 35 U.S.C. § 371 of International Application No. PCT/EP2015/064794, filed Jun. 30, 2015, which claims the priority of European Application No. 14306088.7 filed on Jul. 3, 2014.

The present invention relates to 2-(2-methylamino-pyrimidin-4-yl)-1H-indole-5-carboxylic acid [(S)-1-carbamoyl-2-(phenyl-pyrimidin-2-yl-amino)-ethyl]-amide for use in the treatment of pain associated with osteoarthritis in the knee in patients with effusion.

The compound 2-(2-methylamino-pyrimidin-4-yl)-1H-indole-5-carboxylic acid [(S)-1-carbamoyl-2-(phenyl-pyrimidin-2-yl-amino)-ethyl]-amide (hereinafter referred to as compound A) and preparative methods are described for example in WO2004022553 and WO2013083553. Compound A is an IKKβ inhibitor. The document WO2004022057 describes the use of IKKβ inhibitors for the treatment of various chronic and acute pains, among which pain associated with osteoarthritis, rheumatoid arthritis, chronic musculoskeletal diseases etc.

Osteoarthritis (OA) is the most prevalent form of arthritis worldwide, a major cause of joint pain and disability and the most common reason for total hip and knee replacement. It is estimated that almost half of the adult population of the USA will have symptomatic knee OA by the age of 85, with the highest risk among those that are obese. OA has huge economic implications due to an increasing number of joint replacements, increasing hospital charges and an ageing population. Osteoarthritis is the leading cause of disability in the elderly, affecting the knees, hips, low back, neck and hands. It is characterized by cartilage destruction, new bony growth, pain, joint deformity and loss of function. Once considered a result of mechanical wear and tear, the pathogenesis is now viewed as a complex interplay of genetic, metabolic, biochemical and biomechanical factors with secondary components of inflammation (Sun B H, Wu C W, Kalunian K C (2007), Rheum Dis ClinN Am 33: 135-148).

OA symptoms however frequently include joint pain, swelling and stiffness, suggestive of at least local inflammation. Over recent years, attention has turned to the importance of synovitis in OA, although OA is not traditionally considered a classical inflammatory arthropathy, due to the relative lack of neutrophils in the synovial fluid and the lack of systemic manifestations of inflammation.

It is now recognized that synovitis is common in OA, both in early and late OA and this offers a potential target for treatment, both for symptom and potential structure modification (Ther Adv Musculoskel Dis (2010) 2(6) 349-359; Hayashi et al. Arthritis Research & Therapy 2010, 12:R172).

However, there is still a real lack of safe and effective treatments for OA, barring surgery and acetaminophen, and further treatments are desperately required. As there are currently no disease limiting or restorative therapies, treatment options for OA are mainly based on providing symptomatic (ie, pain) relief. However, none of these is ideal considering their benefit/risk profiles. Main treatments also include weight reduction and exercise, as well as oral and local NSAIDs/COX-2 drugs. However many patients do not tolerate NSAIDs well and/or have contra-indications to NSAIDs. Steroids intraarticular are effective for knee OA including patients with effusions, but have a short duration of effect (1-3 weeks) and can only be administered maximum 4 times a year.

Therefore, even for symptomatic relief alone, there remains an unmet medical need for a safe, effective and well-tolerated treatment of osteoarthritis-associated pain, especially in patients with effusion.

The NFkB pathway is unique in its complex and rapid activation mechanism, the wide variety of inducing stimuli and the large number of genes it regulates. NFkB signaling functions in essentially all mammalian cell types and is activated in response to injury, infection, inflammation, stressful conditions, and is thus involved in the pathogenesis of several human diseases like OA and rheumatoid arthritis (Roman-Bias J A, Jimenez S A (2006). NFkB as a potential therapeutic target in osteoarthritis and rheumatoid arthritis. Osteoarthritis Cartilage 14: 839-848).

The IkB kinase (IKK) is the key enzyme within the "classical" NFkB pathway. IKK is a high molecular weight complex (~700-900 kD) composed of two catalytic subunits, IKKβ (IKK2) and IKKα (IKK1), and a regulatory component NEMO (IKKγ). Pro-inflammatory stimuli, such as IL1β, LPS and TNFα, activate IKK that in turn phosphorylates the Inhibitor of NFkB (IkB) at Ser32 and Ser36 leading to its degradation via the ubiquitin proteasome pathway. Degradation of IkB releases the transcription factor NFkB, which translocates into the nucleus and induces expression of a variety of disease-related genes (e.g. IL1β, TNFα, COX2, -5-LOX, MMPs, ICAM) involved in inflammation, pain and tissue degradation. Studies in animals have shown that IKK activation is a crucial event in the initiation of synovitis.

Therefore, inhibition of IKK should result in a reduction of pro-inflammatory cytokines (e.g. IL1β. TNFα) and of enzymes generating pain mediators (e.g. COX2, 5-LOX) and makes IKK an interesting target for therapeutic intervention of joint pain, which is one of the major symptoms in OA.

During clinical trials with compound A, which is a potent and selective IKKβ inhibitor, it has been observed that this compound has a significant effect in patients suffering from pain associated with an effusion at baseline, upon WOMAC assessment (Western Ontario MacMaster), which evaluates pain, stiffness and physical function using a 5-point Likert scale.

The present invention thus relates to 2-(2-methylamino-pyrimidin-4-yl)-1H-indole-5-carboxylic acid [(S)-1-carbamoyl-2-(phenyl-pyrimidin-2-yl-amino)-ethyl]-amide for use in the treatment of pain associated with osteoarthritis in the knee in patients with effusion.

The present invention relates to 2-(2-methylamino-pyrimidin-4-yl)-1H-indole-5-carboxylic acid [(S)-1-carbamoyl-2-(phenyl-pyrimidin-2-yl-amino)-ethyl]-amide for use in the treatment of pain associated with osteoarthritis in the knee in patients with effusion and/or synovitis, in particular with effusion and synovitis, as assessed by the WOMAC index score.

The present invention also relates to 2-(2-methylamino-pyrimidin-4-yl)-1H-indole-5-carboxylic acid [(S)-1-carbamoyl-2-(phenyl-pyrimidin-2-yl-amino)-ethyl]-amide wherein it is administered as a single intra-articular dose. This single intra-articular dose can range from 15 to 60 mg, in particular 60 mg.

The current invention also relates to a pharmaceutical composition comprising an effective amount of 2-(2-methylamino-pyrimidin-4-yl)-1H-indole-5-carboxylic acid [(S)-

1-carbamoyl-2-(phenyl-pyrimidin-2-yl-amino)-ethyl]-amide as active ingredient and pharmaceutically acceptable excipients.

An effective amount can be from 15 to 60 mg, in particular 60 mg.

Examples of pharmaceutical compositions are suspensions for intra-articular injection and lyophilized cakes that need to be reconstituted in water for injection for intra-articular administration.

According to another of its aspects, the present invention also relates to a method for treating pain associated with osteoarthritis in the knee in patients with effusion and/or synovitis as indicated above, which comprises the administration, to a patient, of an effective dose of compound A or a pharmaceutically acceptable salt thereof.

Other subject matters of the invention are the methods of treatment for the different aspects of the invention described before and the methods of treatment comprising the uses of compound A in patients as described before.

In another aspect, the invention is related to an article of manufacture comprising a packaging material, compound A and a label or package insert contained within the packaging material indicating that patients receiving the treatment with the above mentioned pharmaceutical composition can be treated for pain associated with osteoarthritis in the knee in patients with effusion.

Definitions

Compound A is 2-(2-methylamino-pyrimidin-4-yl)-1H-indole-5-carboxylic acid [(S)-1-carbamoyl-2-(phenyl-pyrimidin-2-yl-amino)-ethyl]-amide having the structure of formula I:

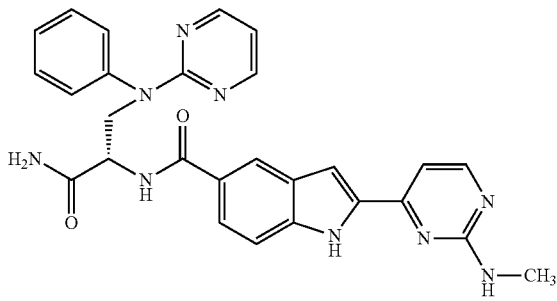

I

Osteoarthritis (OA) is the most common form of arthritis, affecting the knees, hips, hands and spine. It is associated with aging and involves the loss of cartilage which protects and covers the surface of the bone. Common symptoms include pain, stiffness and sometimes swelling, known as an effusion, which results from the accumulation of excess fluid in the joint.

Pain associated to osteoarthritis (OA pain) is a common symptom of osteoarthritis which is typically worse with activity.

Joint effusion (effusion) is the presence of increased intra-articular fluid which results from the accumulation of excess fluid in the joint and which can cause a swelling around the joint, for example the knee. The presence of an effusion in the knee can be determined for example by ultrasound examination of the knee joint (Ann Rheum Dis 2005, 64:1703-1709; Ann Rheum Dis 2005, 64:1710-1714) and/or physical examination like the dancing patellar test (Klaus Buckup, Clinical Tests for the Musculoskeletal System, 2008 Thieme, 2nd edition, pages 202-203).

Synovitis is an inflammation of the synovial membrane. The normal synovium is composed of 1 to 4 layers of cells which merge on their deep surface with a zone of arranged fibrocollagenous tissue containing adipocytes, fibroblasts, mast cells and macrophages. The synovial membrane has an abundant blood and nerve supply running throughout the loose fibrocollagenous tissue. In OA it ranges from marked hyperplasia of the lining layer, with a dense cellular infiltrate composed largely of lymphocytes and monocytes, through to a synovial membrane which is thickened by fibrotic tissue. Surface fibrin deposition and fibrosis within the synovium is common in OA, particularly in the later stages. The synovitis seen in OA knees tends to be diffuse and is generally not localized to areas of chondral defects, although an association has been reported between chondral defects and associated synovitis in the medial tibiofemoral compartment of the knee.

Western Ontario MacMaster (WOMAC) index score evaluates pain, stiffness and physical function using a 5-point Likert scale, with 5, 2 and 17 questions, respectively. This is a widely used measure of symptoms and physical disability originally developed for people with OA of the hip and/or the knee (Bellamy N. Osteoarthritis—An evaluative index for clinical trials. MSc Thesis. McMaster University, Hamilton, Canada. 1982; Bellamy N. et al. J. Rheumatol. 1988; 15: 1833-1840). The Likert version of the WOMAC is rated on an ordinal scale of 0 to 4, with lower scores indicating lower levels of symptoms or physical disability. Each subscale is summated to a maximum score of 20, 8, and 68, respectively. There is also an index score or global score, which is most commonly calculated by summating the scores for the 3 subscales. A visual analogue scale (VAS) version of the WOMAC is also available. The questionnaire is self-administered and takes 5 to 10 minutes to complete.

"Patient" means a human.

"Treating" or "treat" or "treatment" refers to either preventing, providing symptomatic relief, or curing the patient's disease, disorder or condition.

"Therapeutic amount/effective amount" means enough of a compound which becomes available through the appropriate route of administration to treat the patient for the disorder, the condition or the disease.

In some embodiments, the administration can be done either in the morning or in the evening, just before a sleep period, or at any time of the day.

However in specific cases, different dosages may be appropriate; these dosages are comprised within the scope of the present invention. According to usual practice, the dosage suitable to each patient is determined by the physician according to, for example, the administration route, the weight and response of the patient.

LIST OF ABBREVIATIONS

AE: Adverse event
ALT: Alanine aminotransferase
CI: Confidence interval
HA: Hyaluronic acid
hsCRP: High sensitivity C-reactive protein
IKKβ: Inhibitor of nuclear factor kappa-B kinase subunit beta
INR: International Normalized Ratio
MRI: Magnetic resonance imaging
NF-κB: Nuclear factor-kappa B
NSAIDS: Nonsteroidal anti-inflammatory drugs OA: Osteoarthritis
SF: Synovial fluid
TEAE: Treatment-emergent adverse event
WOMAC: Western Ontario MacMaster

FIGURES

FIG. 1: Summary plot of WOMAC subscore for pain (absolute change from baseline) by treatment—efficacy population FIG. 2: Summary plot of WOMAC subscore for pain (absolute change from baseline) by treatment and effusion at baseline—efficacy population The instant invention is illustrated by the clinical data below.

EXAMPLE 1: CLINICAL TRIAL TO ASSESS THE CLINICAL EFFICACY OF A SINGLE DOSE OF COMPOUND A IN RELIEVING SYMPTOMS OF PATIENTS WITH KNEE OA

The objective of this study was to assess in patients with knee OA, the efficacy, safety and tolerability of a single intra-articular dose of Compound A.

This was a two-center, double-blind, randomized, placebo controlled, single dose study. Following a review of the safety data up to Day 28 from Part 1 of this study, the second part of the study assessed the efficacy of a single dose of Compound A, selected from the maximum administered/tolerated dose from Part 1 (60 mg), in relieving symptoms of patients with knee OA.

Screening was performed within 28 days of dosing. Following the single dose of study medication administered via intra-articular injection on Day 1, each patient remained at the Study Unit for 4 hours after dosing and, provided there was no difficulty with tolerability, patients were discharged and returned periodically for outpatient visits. Each patient was followed up to Day 168 (end-of-study visit); therefore the study period was 28 weeks.

Compound A was supplied as a lyophilized cake (to be reconstituted in water for injection for intra-articular administration) in vials containing 20, 40 and 80 mg total of active Compound A. The placebo was commercially available 0.9% saline solution for the injection.

Safety was assessed by adverse event (AE) monitoring, standard clinical laboratory evaluations, physical examination, vital sign and electrocardiogram (ECG) assessments, local tolerability at site of injection and assessments of the knee joint (effusion/worsening of effusion).

The following sub-scales from the WOMAC Index were used to assess the activity of the drug upon pain, stiffness and physical function. Each item will be rated on the basis of the patient's symptoms over the last 48 h, by means of a 5 point Likert Scale: none, mild, moderate, severe, or very severe.

1. Pain Subscale
Five Items:
i. Pain on walking,
ii. Pain while climbing stairs,
iii. Pain at night,
iv. Pain at rest,
v. Pain while weight bearing.
2. Stiffness Subscale
Two Items:
i. Morning stiffness,
ii. Stiffness later in the day.
3. Physical Function Subscale
Seventeen Items:
i. Descending stairs,
ii. Ascending stairs,
iii. Rising from sitting,
iv. Standing,
v. Bending to floor,
vi. Walking on the flat,
vii. Getting in or out of car,
viii. Going shopping,
ix. Putting on socks,
x. Rising from bed,
xi. Taking off socks,
xii. Lying bed,
xiii. Getting in or out of the bath,
xiv. Sitting,
xv. Getting on or off toilet,
xvi. Heavy domestic duties,
xvii. Light domestic duties.

The primary endpoint was the WOMAC Pain sub-scale at Day 56 for evidence of efficacy (change from baseline).

Inclusion criteria are:
Diagnosis of primary knee osteoarthritis, based upon the following:
  X-ray or MRI evidence within the last 6 months for joint space narrowing and osteophyte formation—patients will be Kellgren and Lawrence classification II/III,
  Total WOMAC score 24-72 and
  Fulfilling the American College of Rheumatology Clinical and Radiographic criteria for OA.

Exclusion criteria are:
Patients younger than 40 years,
Women of child bearing potential (For inclusion, women should be either sterilized for more than 3 months or post-menopausal for more than 12 months. Menopause is defined as over age of 60 years or being amenorrheic for at least 2 years with plasma FSH level >30 IU/L.),
Any uncontrolled, chronic condition or laboratory finding which, in the opinion of the Principal Investigator, could potentially put the patient at increased risk,
Abnormal coagulation parameters: outside the range INR 0.85-1.14, activated partial thromboplastin time >33 sec, platelets <140×109/L,
Moderate to severe renal impairment—estimated creatinine clearance (Cockroft-Gault)<50 mL/min,
Underlying hepatobiliary disease and/or elevated ALT>2 ULN,
hsCRP>2 ULN,
Haemoglobin <10 g/dL, white blood cell count (WBC) <3×109/L,
Secondary osteoarthritis: e.g., autoimmune disease, joint dysplasia, aseptic osteonecrosis, acromegaly, Paget's disease, Ehlers-Danlos Syndrome, Gaucher's disease, Stickler's syndrome, joint infection, haemophilia, haemochromatosis, calcium pyrophosphate deposition disease, or neuropathic arthropathy, whatever the cause,
Presence of local skin abnormality at the affected knee joint,
Intra-articular injection within 3 months,
Unable to be maintained for at last 2 weeks prior to entry into study on paracetamol or metamizole as analgesic (after Day 84 patients may be given a nonsteroidal anti-inflammatory drug if necessary to provide better control of OA symptoms), Any Investigational Product within 3 months or
Any patient unlikely to comply with the requirements of the study.

Analysis of Efficacy Variables:

Using the primary analysis efficacy population and for WOMAC sub-score for pain on Day 56, treatment mean differences (Compound A minus placebo) in change from baseline and their one-sided 95% upper limit of the confidence interval were computed using linear fixed effects models with fixed terms for treatment group and sex, and with an unstructured R variance/covariance matrix on treatment group for patient within sex blocks, using SAS Proc Mixed®. In case of convergence problems, other variance-covariance structures were explored.

Description of Efficacy Variable(s):

The signs and symptoms of OA were measured with a standard instrument as WOMAC index.

WOMAC index consists of 24 questions in 3 dimensions subscales:
Pain subcale (5 items)
Stiffness subscale (2 items)
Physical function subscale (17 items)

Each item was rated by means of a 5 point Likert scale: none (=0), mild (=1), moderate (=2), severe (=3) and very severe (=4) A total WOMAC score and a WOMAC subscore for each dimension was calculated.

Analyses of Treatment Mean Differences in WOMAC Scores:

A supportive analysis to the primary analysis was conducted over patients from the efficacy population and with at least one post-dose WOMAC sub-score measurement, using a last observations carried forward (LOCF) approach up to Day 56.

The total WOMAC score and WOMAC sub-score for stiffness and physical function were analysed in the same way as for the primary analysis of WOMAC sub-score for pain.

The treatment mean difference between groups with their one-sided 95% upper limit of the CI was estimated for all other days for all scores. Time profile plots of treatment mean differences with their one-sided 95% upper limit of the CI were provided.

For each WOMAC score (total and sub-scores), the effect size based on the estimated (within the fixed effects model frameworks) mean treatment difference in change from baseline between groups (active versus placebo) were provided at each day with their corresponding 95% CI.

Results:

Safety:

The safety analysis was based on the review of descriptive statistics and individual data for AEs, clinical laboratory, vital signs, and ECG parameters. Adverse events were coded according to the Medical Dictionary for Regulatory Activities (version 15.1) and the numbers of subjects with treatment-emergent AEs (TEAEs) were tabulated (counts and percents). For clinical laboratory, vital signs, and ECG data, the analyses of abnormalities were based on the definitions of potentially clinically significant abnormalities (PCSAs; definitions according to version 2.0 dated 14 Sep. 2009). Local tolerance/tolerability at the site of injection was summarized by descriptive statistics.

Single doses of Compound A 60 mg were well tolerated in patients with knee OA. Arthralgia was the most frequent TEAE reported after administration of Compound A or placebo, followed by injection site reactions. Overall there was no difference between Compound A and placebo (0.9% saline) for the reported TEAEs and their severity, including local reactions at the injection site.

The demographic characteristics at baseline are presented in Table 1. Overall mean age and body mass index (BMI) were similar between the two treatment groups and were typical for this patient population. In the overall population, females were somewhat more numerous but the male:female ratio was comparable between the 2 treatment groups; however males predominated in the placebo effusion group.

TABLE 1

Demography and subject characteristics at baseline by treatment and effusion (safety population)

| | Placebo (N = 66) | | | Compound A 60 mg (N = 64) | | |
|---|---|---|---|---|---|---|
| | without effusion (N = 50) | with effusion (N = 16) | All (N = 66) | without effusion (N = 52) | with effusion (N = 12) | All (N = 64) |
| Age (years) | | | | | | |
| Number | 50 | 16 | 66 | 52 | 12 | 64 |
| Mean (SD) | 62.5 (8.2) | 63.1 (8.6) | 62.6 (8.2) | 61.5 (7.6) | 63.7 (7.1) | 61.9 (7.5) |
| Min:Max | 40:77 | 47:77 | 40:77 | 47:81 | 52:74 | 47:81 |
| Sex [n (%)] | | | | | | |
| Number | 50 | 16 | 66 | 52 | 12 | 64 |
| Male | 19 (38.0%) | 11 (68.8%) | 30 (45.5%) | 23 (44.2%) | 6 (50.0%) | 29 (45.3%) |
| Female | 31 (62.0%) | 5 (31.3%) | 36 (54.5%) | 29 (55.8%) | 6 (50.0%) | 35 (54.7%) |
| Race [n (%)] | | | | | | |
| Number | 50 | 16 | 66 | 52 | 12 | 64 |
| Caucasian/White | 50 (100%) | 16 (100%) | 66 (100%) | 51 (98.1%) | 12 (100%) | 63 (98.4%) |
| Asian/Oriental | 0 | 0 | 0 | 1 (1.9%) | 0 | 1 (1.6%) |
| Height (cm) | | | | | | |
| Number | 50 | 16 | 66 | 52 | 12 | 64 |
| Mean (SD) | 169.1 (8.8) | 173.1 (8.7) | 170.1 (8.9) | 170.8 (11.0) | 169.4 (10.1) | 170.5 (10.8) |
| Min:Max | 151:192 | 160:190 | 151:192 | 147:199 | 156:184 | 147:199 |

TABLE 1-continued

Demography and subject characteristics at baseline by treatment and effusion (safety population)

| | Placebo (N = 66) | | | Compound A 60 mg (N = 64) | | |
|---|---|---|---|---|---|---|
| | without effusion (N = 50) | with effusion (N = 16) | All (N = 66) | without effusion (N = 52) | with effusion (N = 12) | All (N = 64) |
| Weight (kg) | | | | | | |
| Number | 50 | 16 | 66 | 52 | 12 | 64 |
| Mean (SD) | 85.84 (16.64) | 87.86 (11.94) | 86.33 (15.57) | 81.98 (17.57) | 84.53 (17.62) | 82.46 (17.47) |
| Min:Max | 55.7:140.9 | 67.5:109.0 | 55.7:140.9 | 48.3:137.4 | 61.0:116.9 | 48.3:137.4 |
| BMI (kg/m$^2$) | | | | | | |
| Number | 50 | 16 | 66 | 52 | 12 | 64 |
| Mean (SD) | 29.94 (4.94) | 29.42 (4.17) | 29.81 (4.74) | 28.07 (5.47) | 29.49 (6.46) | 28.34 (5.64) |
| Min:Max | 20.1:45.5 | 23.7:36.5 | 20.1:45.5 | 19.7:47.5 | 23.2:48.0 | 19.7:48.0 |

Note:
Patient with effusion is defined as synovial fluid >0 mL, and patient without effusion is defined as synovial fluid = 0 mL or missing.

Efficacy

The primary efficacy endpoint for the study was the effect upon the WOMAC Pain subscore at Day 56. Compound A had neither a clinically significant nor a statistically significant effect on either the WOMAC Pain subscores (FIG. 1 and Table 2) or the other WOMAC subscores or Total score. The effect sizes for WOMAC subscores ranged from 0.12 to −0.04 (negative indicates a positive effect of drug against placebo).

TABLE 2

Summary of statistical analysis of absolute changes from baseline in WOMAC score at Day 56 (efficacy population)

| | Placebo | | Compound A 60 mg | | | Compound A 60 mg vs Placebo | |
|---|---|---|---|---|---|---|---|
| Parameter | N | Estimate | N | Estimate | Estimate | p-value one-sided | Effect size (90% CI) |
| WOMAC subscore for Pain | 66 | −2.2783 | 64 | −1.8229 | 0.4554 | 0.7895 | 0.12 (−0.167 to 0.411) |
| WOMAC subscore for Stiffness | 66 | −0.8833 | 64 | −0.9406 | −0.0573 | 0.4082 | −0.04 (−0.324 to 0.253) |
| WOMAC subscore for Physical function | 66 | −8.4820 | 64 | −7.7966 | 0.6854 | 0.6426 | 0.06 (−0.233 to 0.344) |
| Total WOMAC score | 66 | −11.6062 | 64 | −10.5566 | 1.0495 | 0.6577 | 0.06 (−0.227 to 0.350) |

CI: Confidence interval

However, an additional analysis was carried out for this study in those patients who had an effusion, those from whom SF was removed (varying between 0.2 mL and 113 mL).

Figure 2:
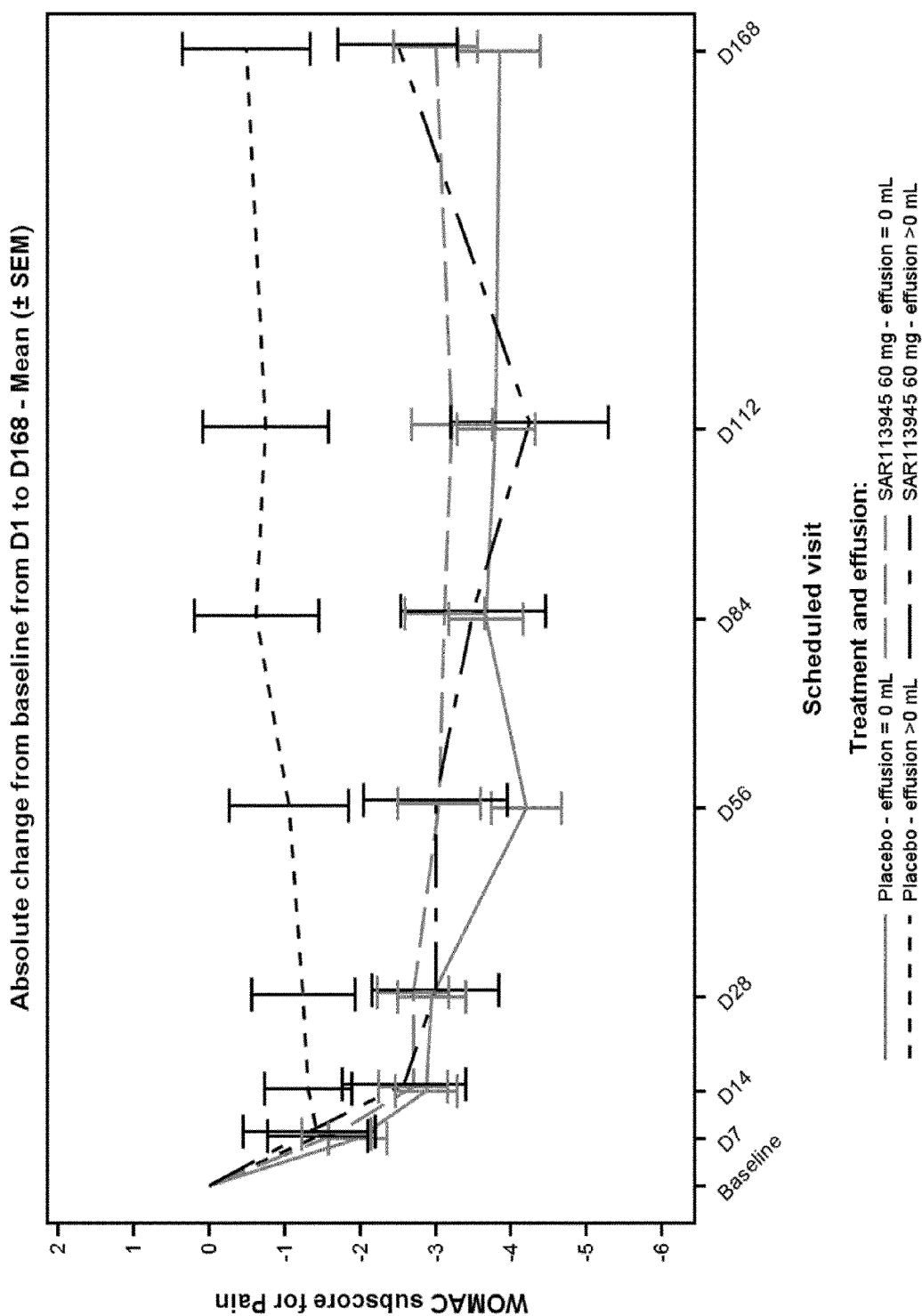

Analysis of the patients with an effusion at baseline (28 patients from the total of 130 [21.5%] was performed (16 patients administered placebo and 12 patients administered Compound A) and showed surprisingly a significant effect of Compound A upon WOMAC Pain score, Total WOMAC score, and WOMAC Physical Function scores at Day 56, corresponding to effect sizes of 0.55, 0.66, and 0.66 respectively (corresponding p-values 0.07, 0.04, and 0.04 respectively), see FIG. 2 and Table 3.

TABLE 3

Summary of statistical analysis of absolute change from baseline in WOMAC score at Day 56-efficacy population for patients with effusion

| Parameter | Placebo N | Placebo Estimate | Compound A 60 mg N | Compound A 60 mg Estimate | Compound A 60 mg vs Placebo Estimate | Compound A 60 mg vs Placebo p-value one-sided | Compound A 60 mg vs Placebo Effect size (90% CI) |
|---|---|---|---|---|---|---|---|
| WOMAC subscore for Pain | 16 | −1.2488 | 12 | −2.9701 | −1.7213 | 0.0745 | −0.55 (−1.189 to 0.092) |
| WOMAC subscore for Stiffness | 16 | −0.2645 | 12 | −1.1672 | −0.9028 | 0.0323 | −0.71 (−1.355 to −0.057) |
| WOMAC subscore for Physical function | 16 | −6.1469 | 12 | −12.9658 | −6.8188 | 0.0434 | −0.66 (−1.300 to −0.008) |
| Total WOMAC score | 16 | −7.7199 | 12 | −17.0761 | −9.3562 | 0.0426 | −0.66 (−1.303 to −0.011) |

CI: Confidence interval
Patient with effusion is defined as synovial fluid >0 mL, and patient without effusion is defined as synovial fluid = 0 mL.

Therefore compound A has demonstrated significant efficacy in a subgroup of patients with OA, i.e patients displaying osteoarthritis in the knee and with effusion; it therefore can be safely used in the treatment of pain associated with osteoarthritis in this subgroup of patients.

The invention claimed is:

1. A method for treating pain associated with osteoarthritis in the knee in a patient with effusion, the method comprising administering to a patient in need of treatment a therapeutically effective amount of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

2. The method of claim 1, wherein the patient also has synovitis.

3. The method of claim 1, wherein the administrating of 2-(2-methylamino-pyrimidin-4-yl)-1H-indole-5-carboxylic acid [(S)-1-carbamoyl-2-(phenyl-pyrimidin-2-yl-amino)-ethyl]-amide comprises a single intra-articular dose.

4. The method of claim 3, wherein the single intra-articular dose comprises 15 to 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

5. The method of claim 3, wherein the single intra-articular dose comprises 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

6. The method of claim 1, wherein the 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof, is administered in a pharmaceutical composition comprising a therapeutically effective amount of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof and a pharmaceutically acceptable excipient.

7. The method of claim 6, wherein the pharmaceutical composition comprises 15 to 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

8. The method of claim 6, wherein the pharmaceutical composition comprises 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

9. The method of claim 2, wherein the administrating of 2-(2-methylamino-pyrimidin-4-yl)-1H-indole-5-carboxylic acid [(S)-1-carbamoyl-2-(phenyl-pyrimidin-2-yl-amino)-ethyl]-amide comprises a single intra-articular dose.

10. The method of claim 9, wherein the single intra-articular dose comprises 15 to 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

11. The method of claim 3, wherein the single intra-articular dose comprises 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

12. The method of claim 2, wherein the 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof, is administered in a pharmaceutical composition comprising a therapeutically effective amount of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof and a pharmaceutically acceptable excipient.

13. The method of claim 12, wherein the pharmaceutical composition comprises 15 to 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

14. The method of claim 13, wherein the pharmaceutical composition comprises 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

15. The method of claim 3, wherein the 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof, is administered in a pharmaceutical composition comprising a therapeutically effective amount of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof and a pharmaceutically acceptable excipient.

16. The method of claim 15, wherein the pharmaceutical composition comprises 15 to 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

17. The method of claim 16, wherein the pharmaceutical composition comprises 60 mg of 2-(2-methylamino-pyrimidin-4-yl)-1H-indole-5-carboxylic acid [(S)-1-carbamoyl-2-(phenyl-pyrimidin-2-yl-amino)-ethyl]-amide, or a pharmaceutically acceptable salt thereof.

* * * * *